US009829435B2

United States Patent
Lu et al.

(10) Patent No.: US 9,829,435 B2
(45) Date of Patent: Nov. 28, 2017

(54) EXTERNAL CAVITY LASER BIOSENSOR ARRANGEMENTS

(75) Inventors: Meng Lu, Champaign, IL (US); Chun Ge, Urbana, IL (US); Brian T. Cunningham, Champaign, IL (US); Stephen Schulz, Lee, NH (US)

(73) Assignees: The Board of Trustees of the University of Illinois, Urbana, IL (US); X-Body, Inc., Waltham, MA (US)

( * ) Notice: Subject to any disclaimer, the term of this patent is extended or adjusted under 35 U.S.C. 154(b) by 1337 days.

(21) Appl. No.: 13/433,619

(22) Filed: Mar. 29, 2012

(65) Prior Publication Data

US 2012/0258549 A1    Oct. 11, 2012

Related U.S. Application Data

(60) Provisional application No. 61/516,793, filed on Apr. 7, 2011.

(51) Int. Cl.
*G01N 21/64* (2006.01)
*H01S 3/1055* (2006.01)
*H01S 5/14* (2006.01)

(52) U.S. Cl.
CPC ..... *G01N 21/6428* (2013.01); *G01N 21/6458* (2013.01); *G01N 2021/6421* (2013.01);
(Continued)

(58) Field of Classification Search
CPC ....... G01N 2021/6421; G01N 21/6428; G01N 21/7743; G01N 2201/0635;
(Continued)

(56) References Cited

U.S. PATENT DOCUMENTS 7,148,964 B2    12/2006  Cunningham et al. ....... 356/326
2004/0151626 A1*  8/2004  Cunningham ........ B01L 3/5085
                                                            435/287.2
(Continued)

OTHER PUBLICATIONS

StackExchange beam splitter description (retrieved on Jan. 4, 2016 from internet <URL: http://physics.stackexchange.com/questions/39577/beam-splitters-direction-of-use).*
(Continued)

*Primary Examiner* — Melanie Y Brown
*Assistant Examiner* — Richard Moerschell
(74) *Attorney, Agent, or Firm* — McDonnell Boehnen Hulbert & Berghoff LLP

(57) ABSTRACT

A label-free biosensor detection arrangement incorporating an external cavity laser (ECL) includes a tunable lasing element (e.g. an antireflection coated laser diode or semiconductor optical amplifier) and a narrow bandwidth resonant reflectance filter as the wavelength-selective element for the tunable lasing element. A sample is deposited on the surface of the resonant reflectance filter containing a biological material. The wavelength emitted by the external cavity laser is continuously tunable by binding interactions between the biological material and the resonant reflectance filter or adsorption of the biological material present in the sample on resonant reflectance filter. The narrow bandwidth resonance reflectance filter can take the form of photonic crystal (PC), a Bragg stack, or a Brag fiber reflection filter.

19 Claims, 12 Drawing Sheets

(52) U.S. Cl.
 CPC .............. *H01S 3/1055* (2013.01); *H01S 5/141* (2013.01); *H01S 5/142* (2013.01)

(58) Field of Classification Search
 CPC ....... G01N 2201/08; G01N 2201/0833; G01N 2201/0846; G01N 33/54373; H01S 3/1055; H01S 5/141; B01L 2300/0654
 See application file for complete search history.

(56) References Cited

U.S. PATENT DOCUMENTS

| | | | | |
|---|---|---|---|---|
| 2005/0018743 | A1* | 1/2005 | Volodin ............. | G02B 27/0944 372/102 |
| 2006/0291766 | A1* | 12/2006 | Schulz ............... | G01N 21/7743 385/12 |
| 2008/0278722 | A1* | 11/2008 | Cunningham ..... | G01N 21/6428 356/317 |
| 2009/0179637 | A1 | 7/2009 | Cunningham et al. ....... | 324/304 |

OTHER PUBLICATIONS

Cunningham & Laing, "Label-free detection of biomolecular interactions: Applications in proteomics and drug discovery," *Expert Rev. Proteomics* 3(3), pp. 271-281 (2006).

Ganesh et al., "Enhanced fluorescence emission from quantum dots on a photonic crystal surface," *Nature Nanotechnology*, vol. 2, pp. 515-520 (2007).

Lu et al., "Label-free biosensor incorporating a replica-molded, vertically emitting distributed feedback laser," *Applied Physics Letters* 92, 261502 (2008).

Cunningham et al., "Label-free assays on the BIND system," *Journal of Biomolecular Screening* 9, pp. 481-490 (2004).

Lu et al, "Plastic distributed feedback laser biosensor," *Applied Physics Letters*, vol. 93, p. 111113, (2008).

Lee et al., "Dual-wavelength external cavity laser with a sampled grating formed in a silica PLC waveguide for terahertz beat signal generation," *Applied Physics B: Lasers and Optics*, vol. 87, pp. 293-296, (2007).

Laurent et al., "Double external cavity laser diode for DWDM applications," *J. Opt. A: Pure Appl. Opt.*, vol. 2, pp. L6-L8, (2000).

Struckmeier, et al., "Electronically tunable external-cavity laser diode," *Optics Letters*, vol. 24, pp. 1573-1574, (1999).

Zambon et al., "Tunable dual-wavelength operation of an external cavity semiconductor laser," *Optics Communications*, vol. 264, pp. 180-186, (2006).

Moskalev et al., "External cavity multiwavelength superbroadband diode laser," *Optics Communications*, vol. 220, pp. 161-169 (2003).

Pokhriyal et al., "Photonic crystal enhanced fluorescence using a quartz substrate to reduce limits of detection," *Optics Express*, vol. 18, pp. 24793-24808, (2010).

Ryu, et al., "High Specificity Binding of Lectins to Carbohydrate-Functionalized Fiber Bragg Gratings: A New Model for Biosensing Applications," IEEE Journal of Selected Topics in Quantum Electronics, vol. 16, No. 3 May-Jun., pp. 647-653 (2010).

Hashimoto et al., "Fiber-Bragg-Grating External Cavity Semiconductor Laser (FGL) module for DWDM Transmission," Journal of Lightwave Technology, vol. 21, No. 9, pp. 2002-2009, Sep. (2003).

Hidalgo et al., "Porous One-Dimensional Photonic. Crystal Coatings for Gas Detection," IEEE Sensors Journal, vol. 10, No. 7, pp. 1206-1212, Jul. (2010).

\* cited by examiner

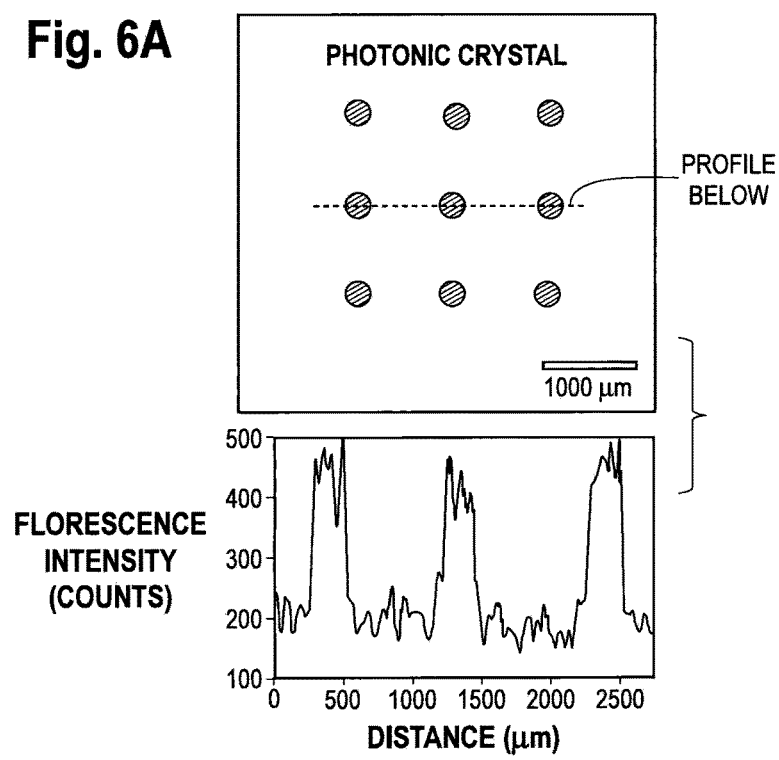
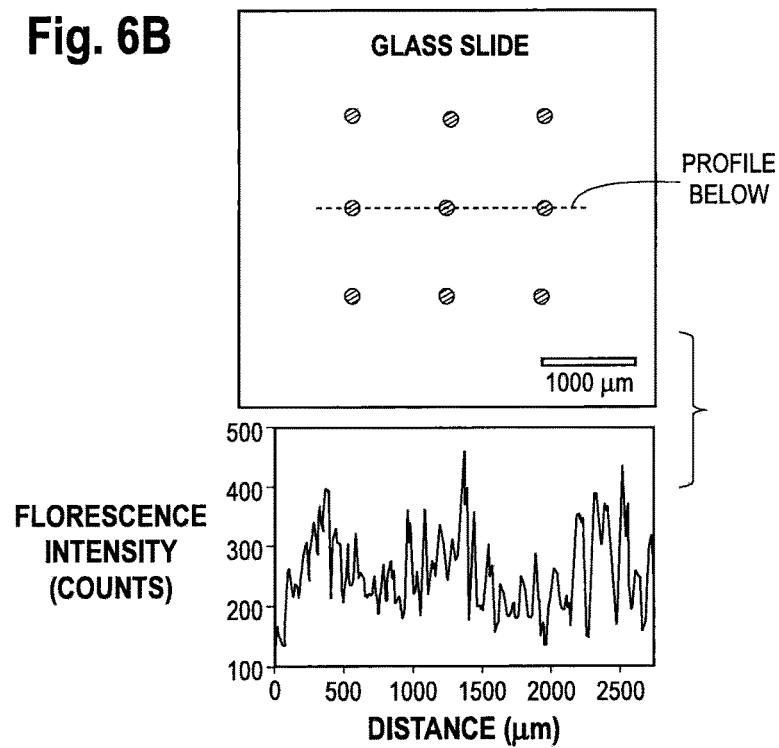

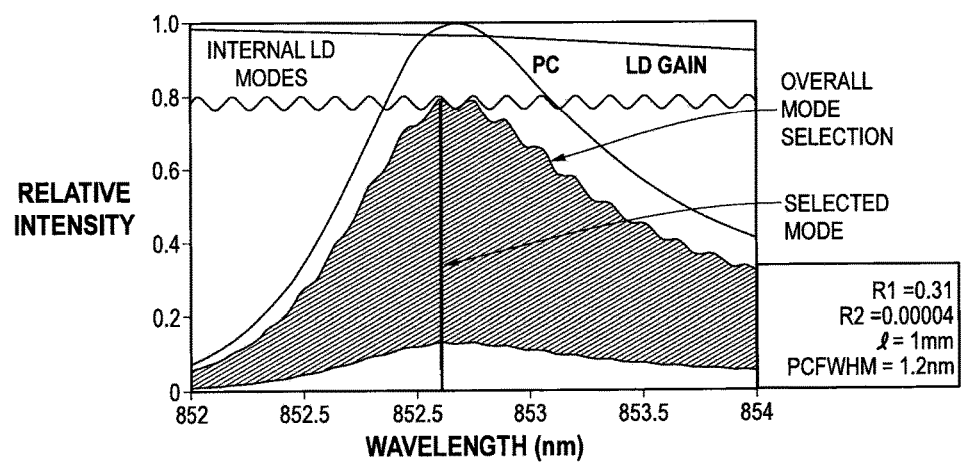
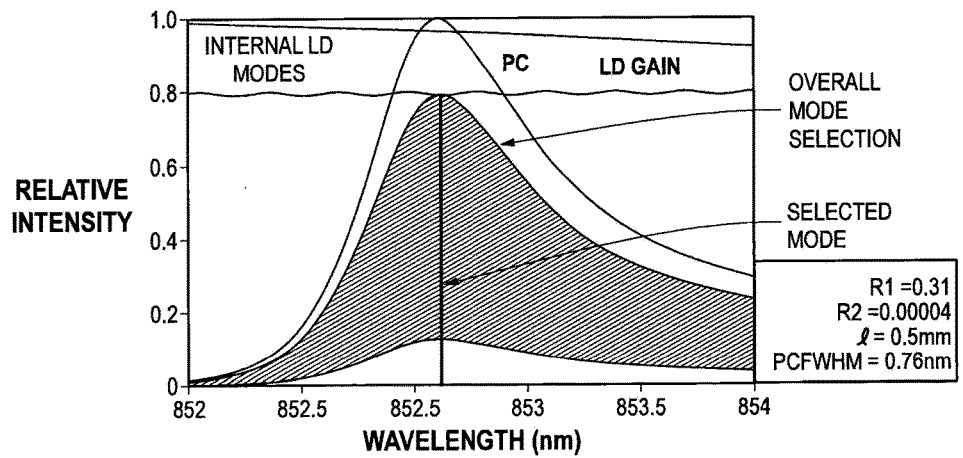

EXTERNAL CAVITY LASER BIOSENSOR ARRANGEMENTS

CROSS-REFERENCE TO RELATED APPLICATION

This application claims priority benefits under 35 U.S.C. §119 to U.S. provisional application Ser. No. 61/516,793 filed Apr. 7, 2011, the content of which is incorporated by reference herein.

BACKGROUND

Label-free biosensors based upon the detection of shifts in resonance wavelength, coupling angle, or the magnitude of optical resonances have become powerful, effective and commercially viable detection and analysis tools for pharmaceutical development, life science research, diagnostics, and environmental monitoring. See Cunningham, B. T. & Laing, L. L., Label-free detection of biomolecular interactions: Applications in proteomics and drug discovery. *Expert Rev. Proteomics* 3, 271-281 (2006); Fan, X. D. et al. Sensitive optical biosensors for unlabeled targets: A review. *Analytica Chimica Acta* 620, 8-26 (2008).

In evaluating the performance of biosensors, resolution is an increasingly important metric, as the ability to reliably measure small shifts in resonant wavelength (or angle) is required for detecting low concentration analytes, small molecule adsorption, and, ultimately, single molecules. In order to build high resolution label free biosensors that can detect small changes in adsorbed mass density, researchers have designed biosensor structures with passive optical resonators having small mode volume and cavity quality factor (Q-factor) values as large as $10^8$, thereby reducing dramatically the shift in resonant wavelength of the sensor that can be reliably resolved. However, for high Q-factor passive resonator biosensors, sensitivity, as measured by the magnitude of wavelength shift, is compromised due to the high degree of confinement of the light inside the cavity. Fundamentally, sensitivity is determined by the strength of interaction between the evanescent electromagnetic field and the adsorbed biomaterial.

Recently, active sensors such as the DFB laser biosensor (DFBLB) have been demonstrated to produce intense and narrow bandwidth emission through the use of stimulated emission, while maintaining high sensitivity by the incorporation of a gain medium within the biosensor structure. See M. Lu et al., U.S. Patent application publication 2009/0179637; Lu, M., Choi, S., Wagner, C. J., Eden, J. G. & Cunningham, B. T. Label free biosensor incorporating a replica-molded, vertically emitting distributed feedback laser. *Applied Physics Letters* 92, 261502 (2008); and Ge, C., Lu, M., Jian, X., Tan, Y. & Cunningham, B. T., Large-area organic distributed feedback laser fabricated by nanoreplica molding and horizontal dipping. *Opt. Express* 18, 12980-12991 (2010).

External cavity diode lasers are described in some detail in the textbook of Ye, C. *Tunable External Cavity Diode Lasers* (World Scientific Publishing Co. Pte. Ltd., 2004). External cavity diode lasers are also described in the following publications: Saliba, S. D. & Scholten, R. E. Linewidths below 100 kHz with external cavity diode lasers. *Appl. Opt.* 48, 6961-6966 (2009); Fleming, M. & Mooradian, A. Spectral characteristics of external-cavity controlled semiconductor lasers. *Quantum Electronics, IEEE Journal of* 17, 44-59 (1981); Hawthorn, C. J., Weber, K. P. & Scholten, R. E. Littrow configuration tunable external cavity diode laser with fixed direction output beam. *Review of Scientific Instruments* 72, 4477-4479, doi:10.1063/1.1419217 (2001); Littman, M. G. & Metcalf, H. J. Spectrally narrow pulsed dye laser without beam expander. *Appl. Opt.* 17, 2224-2227 (1978).

In brief, external cavity lasers ("ECLs") function as a single mode, narrow linewidth, and widely tunable semiconductor laser. A variety of configurations of external cavity lasers are known and described in the *Tunable External Cavity Diode Lasers* textbook. External cavity lasers are used in a wide variety of applications in coherent optical communication systems, ultra-high resolution spectroscopy, sensing, atomic clock timekeeping, and magnetometry. The most striking feature of the external cavity laser is its extremely narrow linewidth. The elongated resonator reduces the damping rate of intracavity light and the spontaneous recombination phase fluctuation, and therefore achieves low phase noise and narrow laser emission linewidth, with values typically below 1 MHz (0.0075 pm). Additionally, the high gain of a semiconductor laser allows for continuous wave operation, which permits simple detection, dynamic monitoring, and an inexpensive, small, robust electrical pump system. Typically, ECL systems utilize first-order diffraction from a grating to provide the optical feedback, as in typical Littrow and Littman-Metcalf configurations. Photonic crystal reflection filters have been demonstrated as efficient wavelength selective mirrors for ECL systems. See Chang, A. S. P. et al. Tunable External Cavity Laser With a Liquid-Crystal Subwavelength Resonant Grating Filter as Wavelength-Selective Mirror. *Photonics Technology Letters, IEEE* 19, 1099-1101 (2007).

SUMMARY

In a first aspect, a biosensor detection arrangement forming an external cavity laser is disclosed. The arrangement includes a tunable lasing element (which can take the form of an antireflection coated laser diode or a semiconductor optical amplifier) and a narrow bandwidth resonant reflectance filter operating as a wavelength-selective element for the tunable lasing element. The wavelength of the tunable lasing element is continuously tunable by a binding interaction between a biological material present in a sample and the resonant reflectance filter or adsorption of the biological material present in the sample on resonant reflectance filter. The biological material may for example be DNA, RNA, protein, peptides, chemical molecules, virus particles, bacteria, and cells present in a sample deposited on the surface of the resonant reflectance filter. Binding interactions or adsorption between the biological material and the surface of the resonant reflectance filter result in shifts in the wavelength of the tunable lasing element. Such shifts can be detected with suitable instrumentation such as a spectrometer, interferometer or other suitable instrument designed to determine laser emission wavelength. This approach provides a useful biosensor detection arrangement for label-free measurement and/or characterization of biological materials, such as for example determining the presence of a biological material, or quantification of the amount of such materials present in a sample.

In one embodiment, the tunable lasing element takes the form of a laser diode in which a first facet of the laser diode has high reflectance and a second facet of the laser diode has antireflection properties, such as an antireflection coating. The resonant reflectance filter is placed directly in front of the second facet. The arrangement further includes an aspheric lens collimating the light from the laser diode onto the resonant reflectance filter and focusing reflection of light from the resonant reflectance filter back into the laser diode. The resonant reflectance filter has a reflection resonance wavelength that is tunable within a wavelength range designed to overlap with the gain spectrum of the laser diode.

Various uses of the biosensor detection arrangement are contemplated, including use for diagnostic assays, protein biomarker detection, DNA sequencing, and genetic expression analysis. To facilitate such uses, the narrow bandwidth resonant reflectance filter is incorporated into an appropriate testing format, which could be a glass slide (e.g., microscope slide), microarray or multi-well plate, beaker, flask, test tube, inner surface of tubing, microfluidic fluid flow channel, or other format.

In one embodiment, the narrow bandwidth resonant reflectance filter of the ECL comprises a photonic crystal having a substrate, a periodic grating of dielectric material formed on the substrate and a high index of refraction material deposited on the periodic grating. In other embodiments, the narrow bandwidth resonant reflectance filter is in the form of a Bragg stack comprising a stack of alternating materials of high and low index of refraction. In still other embodiments, the narrow bandwidth resonant reflectance filter is in the form of a Bragg fiber reflection filter.

In another aspect, a method of detection biomolecular interactions is disclosed comprising the steps of: providing a external cavity laser in the form of tunable lasing element (e.g., an antireflection coated laser diode or semiconductor optical amplifier) and a narrow bandwidth resonant reflectance filter operating as a wavelength-selective element for the tunable lasing element, depositing a sample containing biological material such as, for example DNA, RNA, protein, peptides, chemical molecules, virus particles, bacteria, or cells, on the surface of the resonant reflectance filter, and wherein the wavelength of the tunable lasing element is continuously tunable by adsorption of or binding of the biological material on the surface of the resonant reflectance filter, and detecting changes in the wavelength of the tunable lasing element due to binding interactions between the biological material and a surface of the resonant reflectance filter.

In one embodiment, the biosensor detection arrangement includes a fiber that carries light between the laser diode and resonant reflectance filter. The fiber operates to increase the cavity length of the external cavity laser and thereby obtaining a narrow gap between adjacent longitudinal modes of the external cavity laser and thereby increase detection resolution.

In one possible embodiment, the external cavity laser biosensor arrangement may be used to detect enhanced fluorescence, in which the sample medium includes a bound fluorescent dye. The laser diode emission spectrum and the resonant reflectance filter spectrum are designed to overlap and also to encompass an excitation bandwidth of the fluorescent dye. The measurement or characterization of the sample may make use of an external sensor arrangement that captures an image of the reflectance filter, such as via a CCD camera as shown in FIG. 9.

In still another aspect, a biosensing method is disclosed comprising the steps of: applying a sample containing a fluorescent dye to the surface of a narrow bandwidth resonant reflectance filter; and obtaining enhanced fluorescence measurements from the narrow bandwidth resonant reflectance filter using an external cavity laser biosensor arrangement. Such fluorescent measurements can be obtained with a suitable external sensor, such as camera capturing an image of the resonant reflectance filter.

In one embodiment the external cavity laser is comprised of a laser diode having a highly reflective first facet, an anti-reflective second facet, and the narrow bandwidth resonant reflectance filter. In another embodiment, the external cavity laser is comprised of a semiconductor optical amplification and narrow bandwidth resonant reflectance filter.

BRIEF DESCRIPTION OF THE FIGURES

FIG. 2 represents plots of lasing behavior characterization of the external cavity laser biosensor detection arrangement of FIG. 1a) in which a photonic crystal (PC) is used as the narrow bandwidth wavelength-selective reflection filter.

FIG. 3 are plots showing a bulk sensitivity characterization of the arrangement of FIG. 1a) in which a photonic crystal (PC) is used as the narrow bandwidth wavelength-selective reflection filter.

FIGS. 6A and 6B are fluorescence images and associated line profiles from the ECL-PC arrangement of FIG. 5 and glass slide immunoassays, respectively, at a concentration of 1.6 pg/ml. The fluorescence images are contrast-adjusted for better visualization of the spots. The PC signal-to-noise ratio is approximately 8 times higher than the ratio for the glass slide immunoassay spots.

FIG. 7 shows plots of relative intensity as a function of wavelength, showing the design of PC (photonic crystal), LD (laser diode), and AR (anti-reflective) coating to enable continuous ECL wavelength tuning.

DETAILED DESCRIPTION

Several examples of preferred and alternative embodiments of the invention are disclosed below for purposes of illustration and not limitation. All questions concerning the scope of the invention are to be determined by reference to the appended claims.

This disclosure describes an external cavity laser (ECL) biosensor detection arrangement that also achieves high quality (Q-) factor through the stimulated emission process, while obtaining optical gain from a source that is external to the biosensor structure.

Figure 1A:
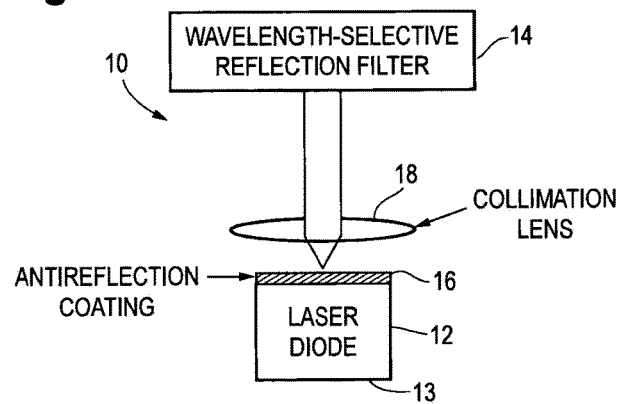
FIG. 1a) is a schematic of the external cavity laser biosensor detection arrangement in accordance with one embodiment of the invention.

Referring to FIG. 1a, a first embodiment of an ECL biosensor detection arrangement 10 is comprised of an antireflection coated laser diode 12 and a narrow bandwidth wavelength-selective resonance reflectance or reflection filter 14. The antireflection coating of the laser diode is shown at 16. The laser diode 12 has a highly reflective facet 13 and an anti-reflective facet 16 in the form of an anti-reflective coating on the facet of the laser 12. The arrangement further includes a collimating lens 18. A sample containing a biological material is deposited on the surface of the filter 14. Binding interactions or adsorption of the biological material on the surface of the sensor causes a shift in the wavelength of the laser diode and this shift is detected by suitable instrumentation, such as a spectrometer or interferometer as explained below.

An alternative arrangement in FIG. 1a is to use a semiconductor optical amplifier in place of the laser diode 12. The SOA is very similar to the laser diode but it has antireflection elements on both ends. The SOA outputs light from its front and back facet, but light from the facet facing away from the sensor is coupled to fiber, reflected from a mirror, and send back into the SOA. The main advantage of a SOA or an conventional A/R coated laser diode is that it has a more flat and broad gain spectrum. With AR coatings on both faces, it does not lase on its own. The use of the SOA avoids having the ECL laser "hopping" between modes that are defined by the gain cavity length.

Figure 1B:
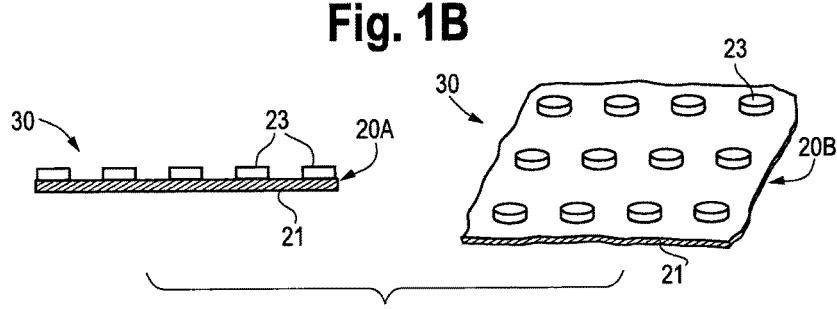
FIG. 1b) illustrates two examples of an external one-dimensional and two-dimensional photonic crystal filter for use as the wavelength-selective reflection filter of FIG. 1a).
Figure 1C:
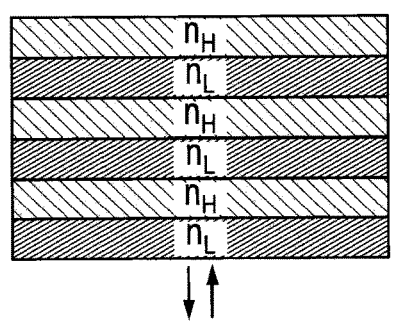
FIG. 1c) is a cross-section of a Bragg stack reflection filter use as the wavelength-selective reflection filter of FIG. 1a).
Figure 1D:
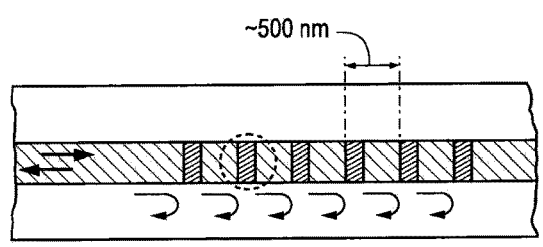
FIG. 1d) is a cross-section of a Bragg fiber reflection filter use as the wavelength-selective reflection filter of FIG. 1a).

Various resonant reflection filters are possible for the wavelength-selective resonance reflection filter 14, such as one- and two-dimensional photonic crystal (PC) resonant filters 20A and 20B, respectively, each of the form of a transparent substrate layer 21 and a dielectric grating 23 having a relatively high index of refraction material (e.g., $TiO_2$) deposited on the grating 23. Bragg stack filter 22 (FIG. 1c), and Bragg fiber reflection filter 24 (FIG. 1d), can also be utilized as the external wavelength-selective reflector filter 14 of FIG. 1a. The Bragg stack and Bragg fiber reflection filter embodiments are described later on.

Preferred embodiments take the form of an external cavity laser 12 with a surface PC resonant reflectance filter (for example, one of the embodiments 20 of FIG. 1b) as the wavelength-selective element 14 of an ECL system. However, the selection of wavelength-selective reflection filter is not limited to only PCs. ECL biosensor systems using filters shown in FIG. 1c-FIG. 1d can be implemented in a similar fashion.

The narrow bandwidth reflectance properties of surface PCs have been extensively studied as wavelength-tunable passive reflectors for label-free biosensor applications. PC biosensors that are fabricated inexpensively over large surface areas from plastic materials using nanoreplica molding methods have been especially advantageous for single-use disposable applications, including incorporation into standard format 96-, 384-, and 1536-well microplates. Cunningham, B. T. & Laing, L. L., Label-free detection of biomolecular interactions: Applications in proteomics and drug discovery. *Expert Rev. Proteomics* 3, 271-281 (2006); Ganesh, N. et al. Enhanced fluorescence emission from quantum dots on a photonic crystal surface. *Nature Nanotechnology* 2, 515-520 (2007). Such designs are also described extensively in the patent literature.

Using a PC filter 20A or 20B (FIG. 1b) as the wavelength selective element 14 of FIG. 1a, single mode ECL emission wavelength is monitored, e.g., with the use of a spectrometer or interferometer (see FIG. 5) to quantify changes in optical density on the PC surface and hence binding or adsorption of a biological material to the surface of the reflection filter 14. Experiments demonstrate that the bulk sensitivity of this detector is $S_b = \Delta\lambda/\Delta n = 212$ nm/refractive index unit (RIU), and single monolayer protein adsorption can readily be observed. The Q-factor of the ECL biosensor output is 1,700, resulting in a Figure of Merit (FOM=$S_b Q$) of FOM=360,000, representing a 25,000× performance improvement over the equivalent passive reflector PC biosensor.

The active medium of the ECL biosensor system is a commercially available antireflection coated laser diode (LD) (FIG. 1a, item 12) (such as item SAL-0850-050, available from Sacher Lasertechnik Group) with a center wavelength of $\lambda=850$ nm and a 3-dB bandwidth of $\Delta\lambda=60$ nm. One facet of the LD has high reflectance (95%) (FIG. 1a at 13) and the other facet is coated with an antireflection layer (FIG. 1a at 16). The PC reflection filter 14/20a is placed directly in front of the antireflection coated facet 16, with an aspheric lens (FIG. 1a, at 18) (d=9 mm, NA=0.55) in between to collimate the light onto the PC, and to focus the reflection from the filter 14 back into the laser diode 12. The PC filter 14/20 has a reflection resonance wavelength that is tunable within a 830<$\lambda$<890 nm range, designed to overlap with the gain spectrum of the LD. When biomolecules adsorb to the PC sensor surface 30 (FIG. 1b), the resonant wavelength of the PC filter will shift to a longer wavelength, which in turn causes a red shift of the ECL emission wavelength. This shift in the ECL emission wavelength is measured by the spectrometer or interferometer of FIG. 5. The high reflection facet (13) of the LD and the PC filter 14/20 together form a Fabry-Perot (FP) cavity. The cavity mode spacing is given by $\Delta\lambda_m \approx \lambda^2/(2 nL)$, where m is the mode number, $\lambda_m$ is the $m^{th}$ resonant wavelength, $\lambda$ is the center wavelength, n is the effective refractive index of the cavity and L is the cavity length. By placing the PC filter L=15 cm away from the LD source, a longitudinal mode spacing of 1.6 pm (picometer) is estimated. The mode spacing ultimately determines the wavelength resolution of the ECL-PC sensor system, representing the smallest increment in wavelength shift that can be measured. In preferred embodiments, the laser emission is collected by an optical fiber, and delivered to a spectrometer with 0.05 nm resolution (model HR4000, available from Ocean Optics), which in this case provides the limitation of the smallest measurable wavelength shift. See FIG. 5 and the discussion below. Such arrangements of using a filter to collect light from a photonic crystal sensor and direct light to a spectrometer are also known in the patent literature.

The PC wavelength selective reflection filter 14/20 can be fabricated using a roll-to-roll nanoreplica molding approach upon a plastic substrate using a design and method described in Lu, M., Choi, S. S., Wagner, C. J., Eden, J. G. & Cunningham, B. T., Label free biosensor incorporating a replica-molded, vertically emitting distributed feedback laser. *Applied Physics Letters* 92, 261502 (2008), and in the patent literature. Briefly, a liquid ultraviolet (UV) curable polymer (Zipcone A, Gelest Inc.) is squeezed between a flexible sheet of polyester film and a silicon master wafer. The silicon master wafer carrying the grating structure was produced by conventional deep UV lithography and reactive ion etching. The transferred gratings have a period of $\Lambda=550$ nm and a depth of d=200 nm. To form a resonant reflectance filter, a 80 nm thin film of $TiO_2$ (refractive index=2.35) was subsequently deposited on top of the replicated grating surface using radio frequency (RF) reactive sputtering. The scanning electron microscope image on the left-hand side of FIG. 6 and the photo below it shows the microstructure of the grating and the PC surface incorporated into a microplate as a testing format.

Figure 2A:
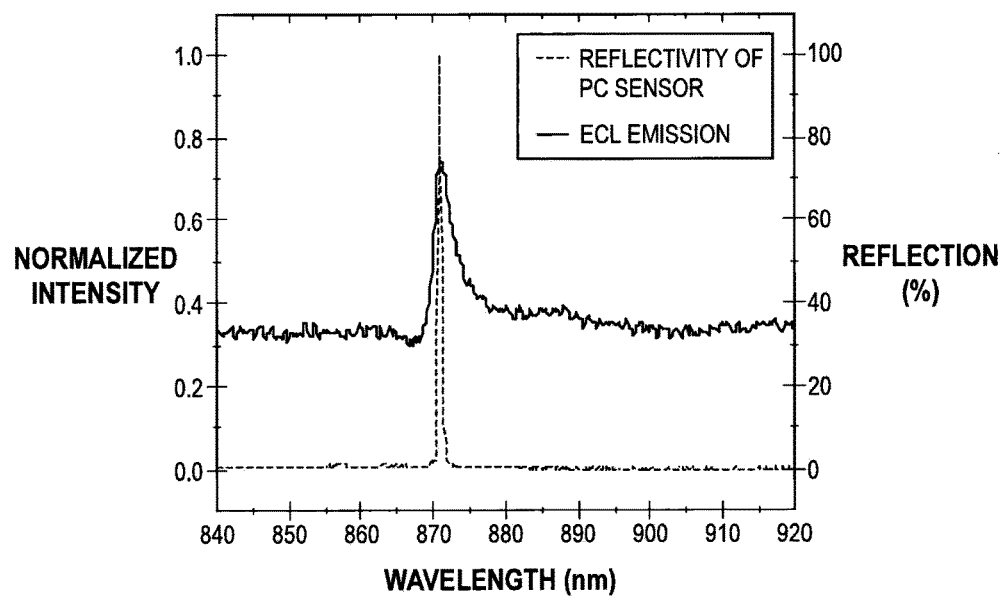
FIG. 2(a) plots the reflection spectrum of the PC filter and laser emission spectrum of the ECL-PC sensor immersed in 50% DMSO solution in water. The laser shows a $\Delta\lambda=0.55$ nm 3-dB linewidth which is limited by the resolution of the spectrometer (0.3 nm), while the PC reflection peak shows a $\Delta\lambda=3.6$ nm full-width-half-maximum (FWHM).

The reflection spectrum of PC filter 14 and the emission spectrum ECL-PC laser 12 in the embodiment of FIG. 1a are shown together in FIG. 2a. Both measurements were taken with the sensor surface (30, FIG. 1b) was exposed to a 50% dimethyl sulfoxide (DMSO) solution in water. The PC filter exhibits a resonance peak with 3-dB bandwidth of $\Delta\lambda=3.6$ nm. While the same PC filter functions as a wavelength selective mirror for the external cavity laser, the 3-dB peak becomes at least as narrow as $\Delta\lambda=0.55$ nm, but is limited by the wavelength resolution of the spectrometer.

Figure 2B:
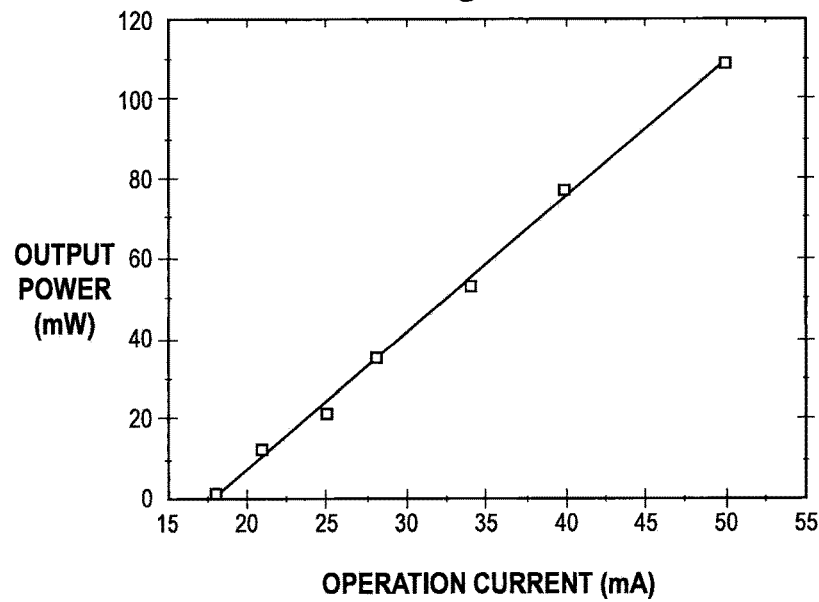
FIG. 2(b) plots the light vs. current (L.I.) curve associated with the external cavity laser. Using a linear least-squares fit to the emission fluence above threshold, clear threshold current of 17 mA and slope efficiency of 3.33 W/A are found.

The relationship between the laser output power and the input current has been investigated. As illustrated in FIG. 2b, using a linear fit to the experimental data, a threshold current of 17 mA and a slope efficiency of 3.33 W/A at 25° C. were found.

Figure 3A:
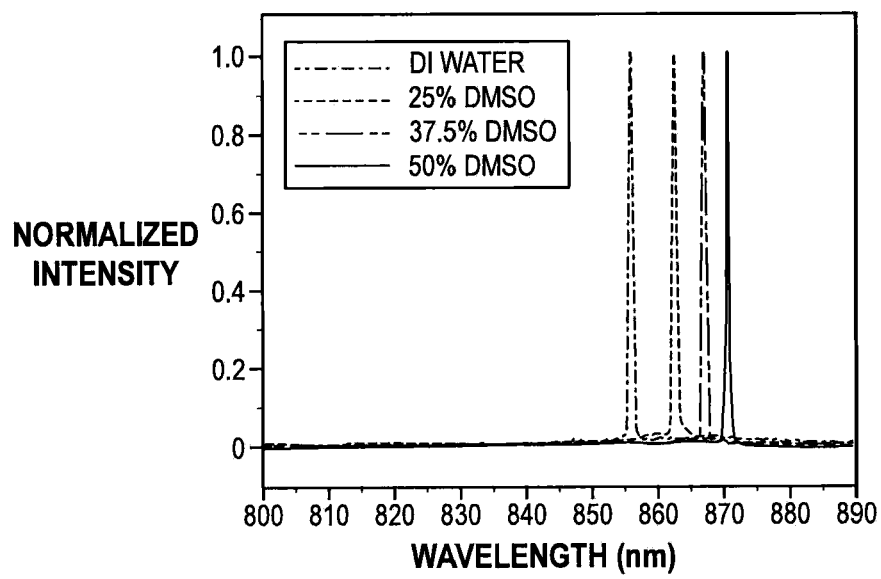
FIG. 3(a) shows the normalized laser emission spectra for the sensor surface in contact with DI water, 25% DMSO, 37.5% DMSO and 50% DMSO solution. The operation current is 19 mA.
Figure 3B:
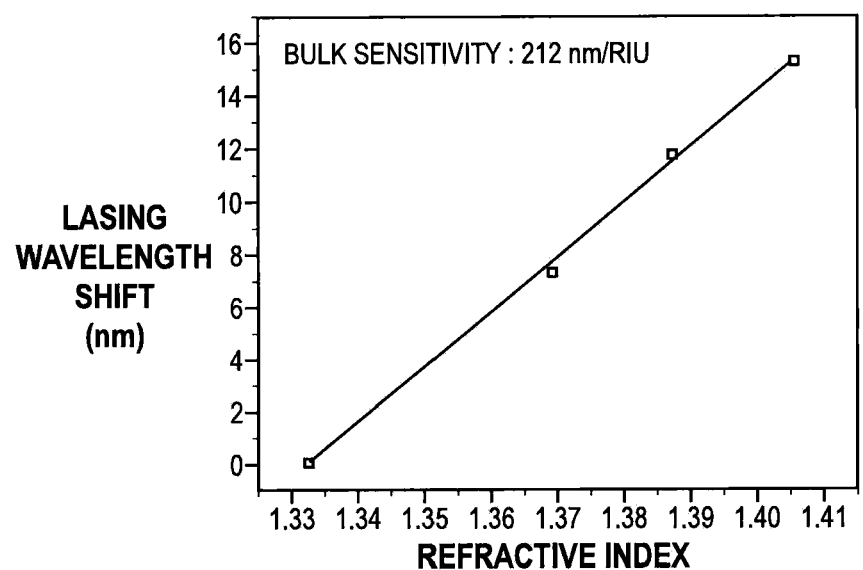
FIG. 3(b) shows the laser emission wavelength shifts of sensor exposed to liquid media with different refractive index. A linear fit to the experimentally obtained data reveals a bulk sensitivity of 212 nm/RIU.

In order to characterize the sensitivity to changes in the refractive index of media in contact with the sensor surface, the PC sensor surface was exposed to four solutions (deionized (DI) water (n=1.333), 25% dimethyl sulfoxide (DMSO) (n=1.369), 37.5% DMSO (n=1.388) and 50% (DMSO) (n=1.406)) to monitor the laser emission wavelength shifts. Single mode laser emissions were measured as shown in FIG. 3a. The bulk refractive index sensitivity of $S_b = \Delta\lambda/\Delta n = 212$ nm/RIU was calculated by plotting the laser wavelength in terms of refractive index of solution, as shown in FIG. 3b.

Figure 4:
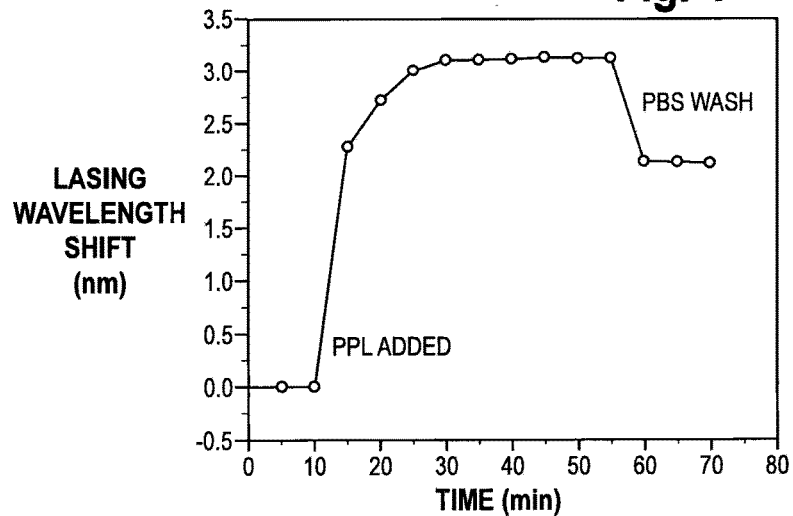
FIG. 4 shows surface sensitivity characterization of the arrangement of FIG. 1, in which a photonic crystal (PC) is used as the narrow bandwidth wavelength-selective reflection filter, as a plot of polymer protein self-limiting monolayer (PPL) absorption induced laser emission wavelength shift.

By monitoring the spectral output of the ECL biosensor over time, the kinetic characteristics of surface mass adsorption of sample material deposited on the surface 30 (FIG. 2b) of the PC filter 14/20 can be recorded. FIG. 4 illustrates the dynamic detection of the growth of a single protein polymer poly (Lys, Phe) (PPL, Sigma-Aldrich) layer. These data were obtained by initially establishing a baseline emission wavelength when the sensor surface was soaked in a phosphate-buffered saline (PBS) solution with pH=7.4. After 10 minutes, the PBS solution was replaced with PPL solution (1 mg/ml) and stabilized for 45 min. Then, the sensor surface was rinsed with PBS solution to remove any PPL that was not firmly attached to the sensor surface. In this manner, the sensor was observed to exhibit an emission wavelength shift of ~2.12 nm for PPL monolayer adsorption, and no drift of the lasing wavelength was detectable over time periods up to one hour.

In summary, a tunable external cavity laser based biosensor has been demonstrated and characterized. The sensor produces a ~6 mW output signal and exhibits a spectral linewidth of 0.55 nm which is limited by the resolution of the spectrometer.

In this illustrated example, the laser emission is collected by an optical fiber, and delivered to a spectrometer with 0.05 nm resolution (HR4000, Ocean Optics), which in this case provides the limitation of the smallest measurable wavelength shift. $Q=3-5\times10^7$ was measured via scanning interferometry. Q is defined as the quality factor, as Q=(wavelength/delta wavelength), where "delta wavelength" is the width of the wavelength spectrum (in nm wavelength) measured at ½ of the maximum amplitude. The laser emission wavelength was ~855 nm, so delta wavelength ~0.0000171 nm.

Bulk refractive index sensitivity of 212 nm/RIU has been demonstrated. The surface sensitivity of the biosensor results in a shift of the lasing wavelength of 2.12 nm when a monolayer of PPL is adsorbed onto the sensor surface. Due to the broad gain spectrum of the laser diode, the ECL biosensor sensor has tuning range as wide as 60 nm. The high intensity, single mode, narrow bandwidth output of the ECL-PC sensor affords the capability for resolving extremely small wavelength shifts, and alternate wavelength measurement instruments (such as interferometers) will increase the resolution of this sensor by detecting yet smaller shifts in the laser wavelength. The ECL-PC sensor detection arrangement is compatible with the commercialized PC sensor system which has been widely used in pharmaceutics high throughput screening, life science research, diagnostic testing, and environmental detection. See Cunningham, B. T. et al. Label-free assays on the BIND system. *Journal of Biomolecular Screening* 9, 481-490 (2004).

The ECL photonic crystal biosensor arrangement described herein offers the following compelling characteristics:

- Excellent sensor Figure of Merit. Based upon typically obtained ECL performance, Q~$3\times10^7$ will be possible (and has been achieved in our preliminary results), which combined with $S_b$=250 nm/RIU for the PC (using a conservative design), results in FOM=$7.5\times10^9$, surpassing SPR by 290,000×, passive PC biosensors by 25,000× and ring resonators by 3,750×.
- The detection instrumentation is robust. The PC surface 30 is illuminated from below at normal incidence without requirement for a coupling prism, tapered optical fiber coupling, or waveguide coupling.
- Detection is easily multiplexed. The PC surface 30 can be "addressed" at any illuminated location, and a single measurement can be obtained in ~5 msec. PC surfaces are already incorporated into 384- and 1536-well standard format microplates (see the inset photograph in FIG. 5), thus a biosensor holder on a lateral translation stage can be operated with the illumination/detection optics to rapidly measure many sensors sequentially. See e.g., U.S. Pat. No. 7,148,964 and the BIND plate reader products available from SRU Biosystems, Inc., Woburn Mass.
- Highly accurate referencing can be implemented. Because the PC surface prevents lateral propagation of light at the resonant wavelength, adjacent locations on the PC surface can be used to provide independent active/reference measurements (for example, from adjacent wells in a microplate). A referencing method is described below for dual-wavelength operation of the ECL.
- Compact illumination source. The laser diode 12 is packaged in a small (9 mm diameter) TO-9 header and integrated with its collimation lens 18 (FIG. 1*a*) by the diode manufacturer. Compact voltage and thermal control modules for diodes used in tunable ECL systems that simply plug into this diode form factor are commercially available from many sources.
- Inexpensive and large area sensor. PC sensors for the present biosensor arrangement are produced by replica molding in plastic materials over large surface areas and incorporated into standard laboratory liquid handling formats such as microplates, microscope slides, microfluidic channels and biomedical tubing. PC surfaces are manufactured by roll-to-roll methods, and are thus inexpensive enough for single use disposable applications in diagnostic testing, high throughput screening, and pathogen sensing. These new system will offer high throughput measurement capability and allow the study of more complicated biomolecule interactions.

Achievable Detection Resolution with ECL Biosensor Arrangements

Figure 5:
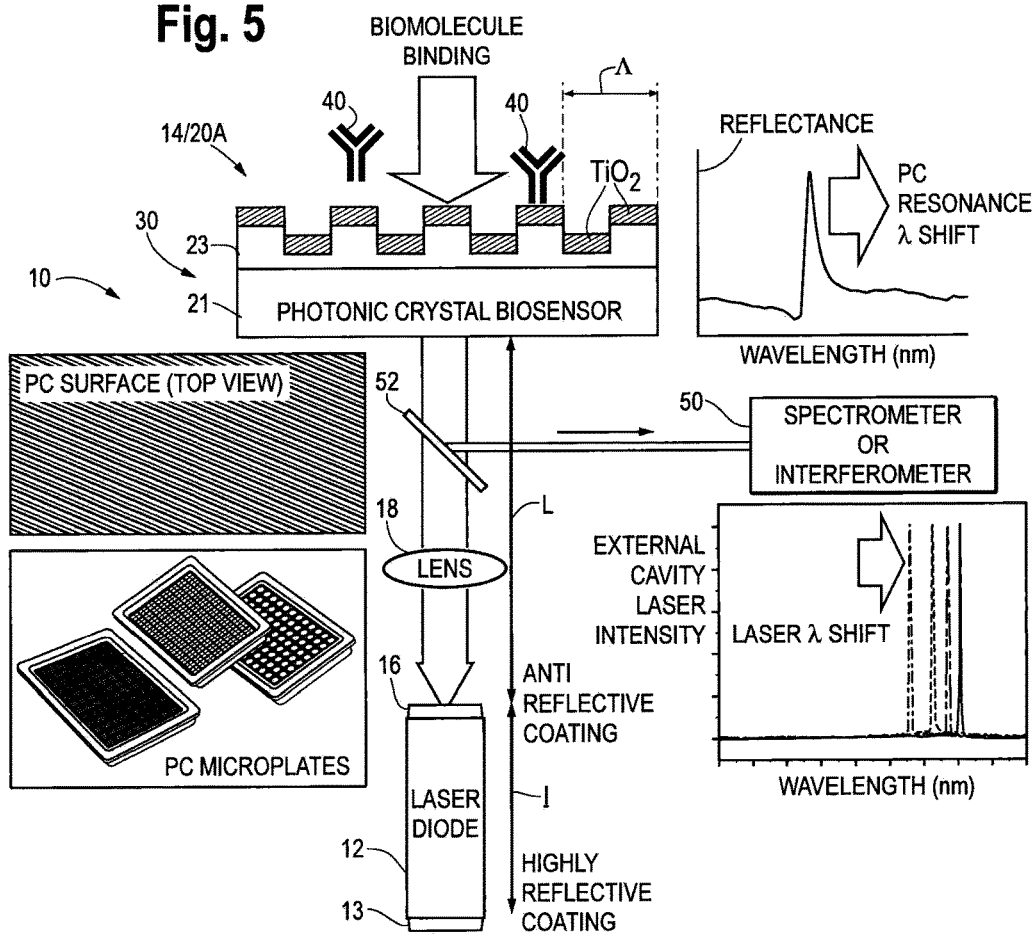
FIG. 5 is a schematic diagram for a second ECL biosensor detection arrangement in accordance with this disclosure in which a wavelength-tunable PC resonant reflection filter serves as the external mirror for an AR-coated diode laser-pumped cavity. Extremely high Q is obtained through the stimulated emission process and gain narrowing of the laser for high resolution biosensing that also maintains high sensitivity. The PC surfaces are sub-wavelength resonant linear gratings designed to form guided mode standing waves at a wavelengths within the gain spectrum of the laser diode. The PCs are fabricated inexpensively over large surface areas and incorporated into testing formats as desired, for example microplates or microscope slides.
Figure 8:
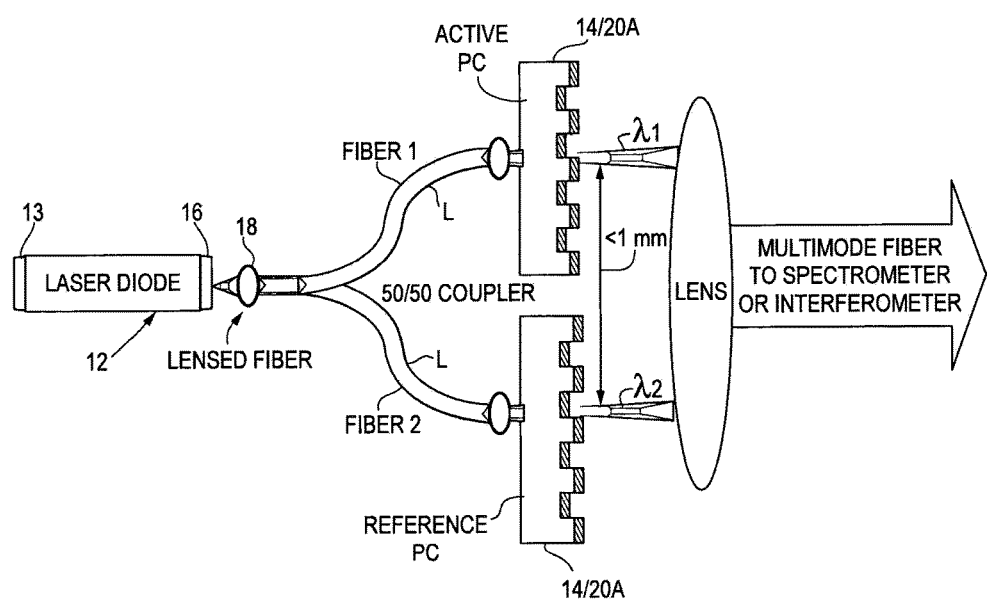
FIG. 8 is a schematic diagram of a system for coupling a single laser diode into two separate external cavities, in which one cavity illuminates the "active" sensor area, and the second cavity serves as a "reference" by illuminating a nearby region of the PC that is not undergoing biochemical binding. External cavity emission will be captured from the front surface of the PC for wavelength measurement by spectrometer or interferometer. If an interferometer is to be used, electronic shutters will be placed between the fiber ends and the PC to enable selection of λ1 or λ2.

As discussed previously, the key to being able to observe small wavelength shifts associated with biomolecular binding to the reflection filter surface lies in obtaining a narrow gap between adjacent longitudinal modes of the ECL. This is achieved by increasing the cavity length L (FIG. 5). The L=15 cm air cavity used to obtain our preliminary results only provides a $\Delta\lambda$=2.5 pm separation between adjacent ECL modes. Therefore, it may be desirable to substantially increase the cavity length. Rather than use an air cavity (as in the embodiment of FIG. 1*a*), a laser diode coupled into a single mode optical fiber may also be used. See FIG. 8. Systems using this approach have been successfully demonstrated for many years (M. Lu, S. S. Choi, U. Irfan, and B. T. Cunningham, "Plastic distributed feedback laser biosensor," *Applied Physics Letters*, vol. 93, p. 111113, 2008; M. Lu, S. S. Choi, C. J. Wagner, J. G. Eden, and B. T. Cunningham, "Label-free biosensor incorporating a replica-molded, vertically emitting distributed feedback laser," *Applied Physics Letters*, vol. 92, pp. 261502-261504, 2008, and fiber-coupled, AR-coated diodes packed in TO9 headers with temperature control may be purchased commercially. Using a 1 m silica fiber, the effective cavity length L (FIG. 8) increases to ~1.45 m, reducing $\Delta\lambda$ to 0.25 pm. The distal end of the fiber may be placed directly in front of the PC surface to reduce losses from beam divergence, as shown in FIG. 8.

Although our preliminary data in the examples disclosed above used a miniature spectrometer to measure the ECL emission, the ability to measure wavelength shifts with 0.25 pm precision with a spectrometer would require a high precision system that would be prohibitive in terms of cost and size. Fortunately, accurate laser wavelength meters using Fizeau interferometers are capable of 100 MHz (=0.3 pm wavelength) resolution, are approximately the size of a shoe box, and weigh ~5 lbs. Using CW illumination, such systems are capable of rapid measurements (150 Hz). While the use of such a system is compatible with implementation of a laboratory bench instrument, exciting results have been shown in the development of highly miniature laser wavelength measurement systems with sub-pm resolution that would eventually make handheld instruments a possibility. See P. Kiesel, O. Schmidt, S. Mohta, N. Johnson, and S. Malzer, "Compact, low-cost, and high-resolution interrogation unit for optical sensors," *Applied Physics Letters*, vol. 89, pp. 201113-201115, 2006. We anticipate the commercial availability of such an approach, although it is not central to the goals of this disclosure. Thus, we specifically contemplate the use of a variety of possible detection instruments to monitor the shift in ECL wavelength to measure binding or adsorption of biological materials on the biosensor surface, including spectrometers, interferometers, and hand-held or laboratory bench top laser wavelength measurement units such as described in the above-reference Kiesel et al. article.

The interaction between the Fabry-Perot modes of the diode-PC cavity, the optical cavity created between the two end facets of the diode, and the PC resonant reflection results in the potential for "mode hopping" that can potentially destroy the ability to reliably obtain smooth transitions between external cavity modes. Mode hopping is a well-known issue for all tunable ECL systems, and a large number of publications discuss its origins and solutions. The basic mechanism for mode hopping is shown graphically via computer simulations of the available modes, in FIG. 7*a*-*b*. In the first configuration (FIG. 7*a*), the diode length is 1.0 mm, the AR coating reflectivity=0.04%, and the PC resonance width is $\Delta\lambda$=1.2 nm, corresponding approximately to the configuration used to obtain our Preliminary Results. The ECL will effectively multiply the diode gain spectrum by the mode profiles of the two cavities to select the lasing wavelength, so a small shift in PC resonant wavelength can either result in a small incremental shift, or hop to a new mode that is ~0.1 nm away. Guided by the literature, shortening the diode to 0.5 mm, reducing the AR coating reflectivity to 0.004%, and reducing the PC resonance width to $\Delta\lambda$=0.5 nm results in the situation shown in FIG. 7*b*, in which wavelength tuning is continuous due to the increased mode spacing between the diode facets and reduction in the magnitude of the intra-diode oscillation strength. These design considerations will drive our selection of components, and we have verified that these diode specifications are available commercially.

The use of semiconductor optical amplifiers allows us to avoid our ECL hopping between modes and for that reason may be preferred to the antireflection coated laser diode as the tunable lasing element in the ECL.

Further Embodiments

A. ECL Biosensors with Self Referencing

Previous publications have demonstrated that a single diode in an ECL cavity can support operation of two or more independent lasing modes. See K. S. Lee, C. S. Kim, R. K. Kim, G. Patterson, M. Kolesik, J. V. Moloney, and N. Peyghambarian, "Dual-wavelength external cavity laser with a sampled grating formed in a silica PLC waveguide for terahertz beat signal generation," *Applied Physics B: Lasers and Optics*, vol. 87, pp. 293-296, 2007; A. Laurent, P. Chanclou, M. Thual, J. Lostec, and M. Gadonna, "Double external cabity laser diode for DWDM applications," *J. Opt. A: Pure Appl. Opt.*, vol. 2, pp. L6-L8, 2000; J. Struckmeier, A. Euteneuer, B. Smarsly, M. Breede, M. Born, M. Hofman, L. Hildebrant, and J. Sacher, "Electronically tunable external-cavity laser diode," *Optics Letters*, vol. 24, pp. 1573-1574, 1999; V. Zambon, M. Piche, and N. McCarthy, "Tunable dual-wavelength operation of an external cavity semiconductor laser," *Optics Communications*, vol. 264, pp. 180-186, 2006; and I. S. Moskalev, S. B. MIrov, V. V. Fedorov, and T. T. Basiev, "External cavity multiwavelength superbroadband diode laser," *Optics Communications*, vol. 220, 2003.

We contemplate a method for dual-wavelength ECL operation for label-free biomolecule detection, in which one wavelength is used for the "active" (i.e. binding assay) sensor, and the second wavelength is used as a "reference" to control against common mode noise sources, such as for example temperature variability. The approach, shown in FIG. 8, uses a laser diode coupled into a fiber that is bifurcated at a point along its length. Each distal end of the bifurcated fiber is used to illuminate a separate region from a PC (resonance reflection filter) surface, where the two regions are immediately adjacent to each other—for example in neighboring wells within a 1536-well PC biosensor microplate. In this case, the two sensor regions can be separated by ~1 mm, and should thus experience nearly identical thermal environments. The active and reference sensors may be immersed in identical liquid media, and also receive identical treatment for surface chemistry, and capture molecule immobilization.

B. Photonic Crystal Enhanced Fluorescence ["PCEF"] with External Cavity Laser Biosensor Arrangements PC surfaces have been demonstrated as a means for enhancing the detection sensitivity and resolution for assays that use a fluorescent tag to quantify the concentration of an analyte protein molecule in a liquid test sample. PC fluorescent excitation enhancement is obtained by designing the PC structure to provide an optical resonance at the same wavelength as a laser that is used to excite a particular fluorescent dye. Compared to illumination of a fluorophore by a laser on an ordinary glass surface, illumination of a PC by a laser at the resonant coupling condition establishes an electromagnetic standing wave that is confined to the PC surface with a magnitude that is 30-50× greater than the illumination source. The enhanced electric field extends into the medium (air or water) that is adjacent to the PC, where its intensity decays exponentially to form a ~100 nm deep evanescent field region. The resonant enhancement may be switched on by illuminating the PC with a collimated laser at the resonant coupling angle, and may be switched off by illuminating at a different incident angle.

PC surfaces offer a second enhancement mechanism called "enhanced extraction." Enhanced extraction is obtained by designing the PC to provide a second optical resonance at the wavelength of fluorescence emission, resulting in a greater proportion of emitted photons being directed near-normal to the PC surface, where they can be gathered efficiently by a detection system. Previous reports of PCEF in which the effects of enhanced excitation and enhanced extraction are shown to multiply result in ~350× overall increase in signal-to-noise ratio for fluorophore-tagged proteins on an appropriately designed PC, compared to detection of the same analyte on an unpatterned glass surface, with a maximum achieved signal enhancement factor of 7500×.

In light of the preceding discussion, we contemplate the use of ECL biosensors as a label-free optical biosensor approach that simultaneously offers high sensitivity and high resolution, while also capable of functioning as a self-tuning platform for photonic crystal enhanced fluorescence. One possible detection approach, shown schematically in FIG. 5, uses the PC surface 30 as one external mirror of an external cavity laser that obtains its gain from a continuous-wave AR-coated laser diode. The diode 12 emission spectrum and the PC 14 resonance spectrum are designed to overlap, resulting in high Q single mode emission that is tuned by absorption of biomaterial 40 on the PC surface 30. High sensitivity is obtained from the large wavelength shifts induced with the PC resonant mode, while high resolution is obtained through the laser stimulated emission process and the operating characteristics of the external cavity. A high precision interferometer or spectrometer 50 is used to detect laser wavelength shifts caused by biomaterial absorption. The spectrometer 50 is coupled to the biosensor arrangement 10 via a beam splitter 52 and glass fiber 54.

Further by way of background and as an example application for PCEF, a microspot fluorescence immunoassay for the cytokine TNF-α was performed simultaneously on glass slides and PC surfaces under identical experimental conditions to evaluate the impact of enhanced fluorescence on the assay. The PC used in this work is similar to the structure shown in FIG. 5, but with a grating period of Λ=360 nm to produce optical resonances near λ=633 nm wavelength. A microspot immunoassay is performed on both glass and PC substrates using a fluorescent Cyanine-5 (Cy5) label, which is excited by illumination with a HeNe laser (λ=633 nm). By evaluating the immunoassay over a concentration series on glass and PCs, the impact of PC enhanced fluorescence on the assay resolution and detection limit is assessed.

A fully detailed description of the chemical reagents, PC fabrication procedure, and epoxy-silane based surface chemistry for covalent attachment of anti-TNF-α antibody are given in P. C. Mathias, N. Ganesh, and B. T. Cunningham, "Application of photonic crystal enhanced fluorescence to a cytokine immunoassay," *Analytical Chemistry*, vol. 80, pp. 9013-9020, 2008. Nine spots of capture antibody (anti TNF-α) were applied to the glass and PC surfaces using a noncontact droplet deposition instrument (Perkin Elmer Piezoarray). Fluorescence measurements were taken using a commercially available confocal microarray scanner with user-adjustable angle of incidence laser excitation (LS Reloaded, Tecan) in order to allow alignment of the PC resonance with the incident wavelength. The PC slides and glass slides were scanned with identical conditions (photomultiplier tube gain, incidence angle). PC slides were scanned at an angle that fulfills the resonant condition at λ=633 nm (3.2°). Array Pro Analyzer software was used to quantify spot and background fluorescent intensities. ImageJ software was used to generate spatial profiles of the fluorescence data.

Figure 6C:
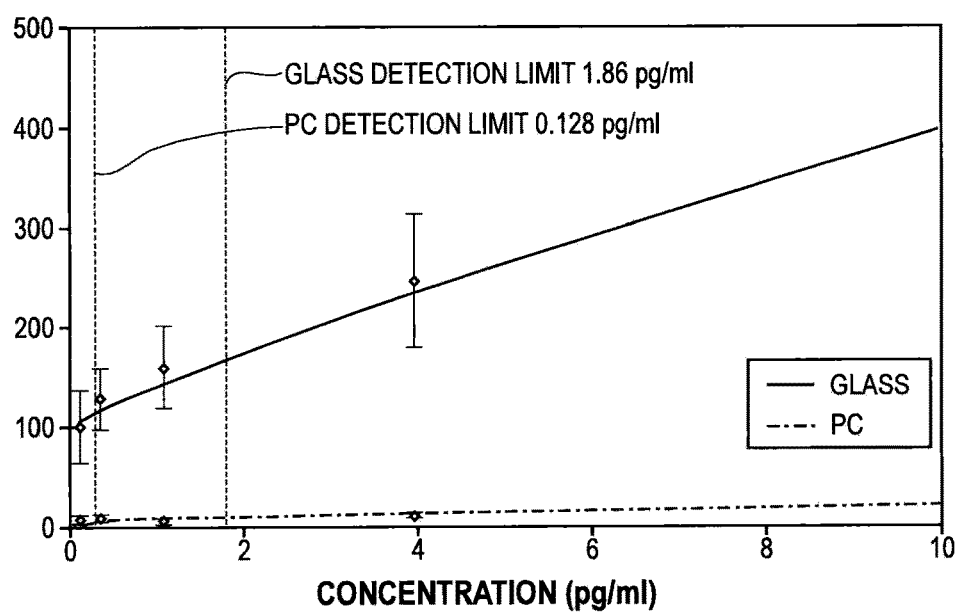
FIG. 6C is a dose-response curve for detection of TNF-α in bovine serum on PC and glass surfaces. Error bars represent standard deviation of 9 replicate spots per concentration, repeated 2× on separate regions of the slide. Limit of Detection (LOD) values were determined by ProMat software.

The enhancements observed in the signal intensities are higher than the increased background and noise intensities, which lead to increased Signal-to-Noise Ratio (SNR). The SNR is the net spot intensity divided by the noise intensity and represents how easily a spot can be differentiated from noise. FIG. 6 illustrates the enhanced SNR for spots incubated at one of the lowest concentrations of TNF-α (1.6 pg/ml), with an estimated SNR enhancement of over 8 times. As an extension of the results shown in FIG. 6, PCEF has been applied to multiplexed biochemical assays including DNA microarrays for gene expression analysis and protein microarrays for detection of cancer biomarkers in the context of disease diagnosis.

An important aspect of all PCEF detection instruments demonstrated to date is that a fixed wavelength monochromatic (i.e. laser) excitation source must illuminate the PC at the resonant coupling angle to excite the resonant electromagnetic standing wave that generates enhanced excitation. This requirement adds complexity to the detection system though the use of angle-tunable mirrors or linear translation of a lens and careful adjustment of the incident angle caused by variations in sensors, surface chemistry density, and capture molecule density. Through the tuning mechanism provided by the external cavity laser, the lasing wavelength of the system will automatically match the PC resonant wavelength at normal incidence, thus removing the requirement for laser angle tuning. Electromagnetic field computer simulations (FIG. 9) predict a substantial enhancement of the electric field intensity in the media immediately adjacent to the PC surface compared to illumination of an ordinary glass surface.

C. Demonstration of PCEF with ECL Biosensors

Figure 9A:
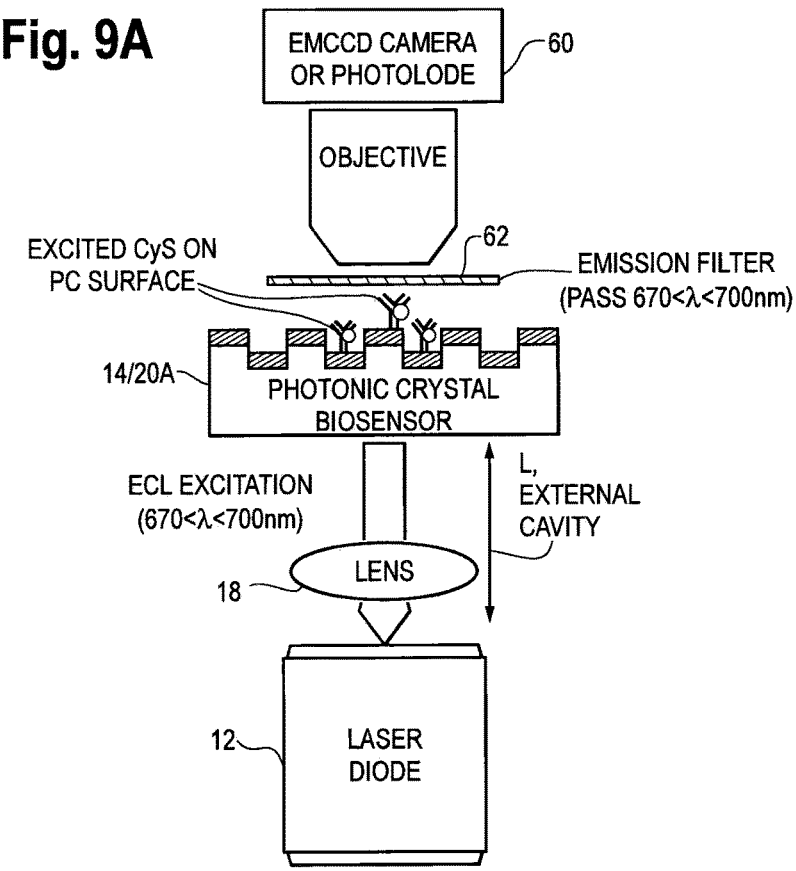
FIG. 9A is a schematic diagram of a biosensor arrangement used to excite and measure PCEF from a PC surface as one end of an external cavity laser.
Figure 9B:
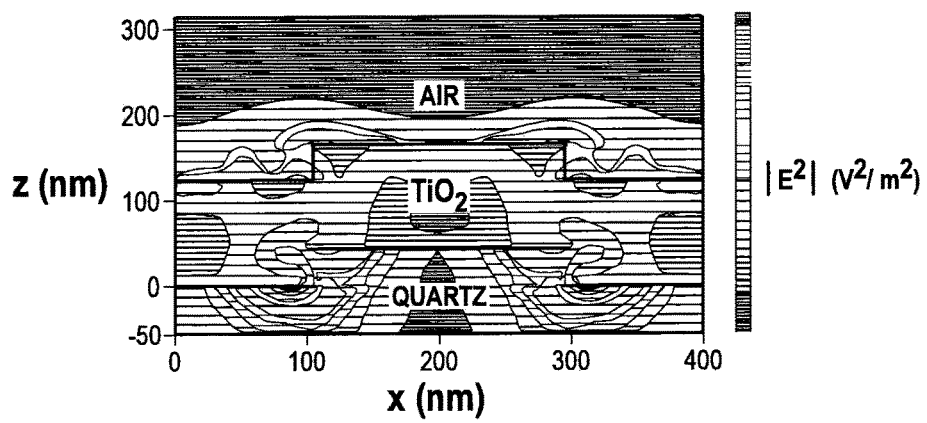
FIG. 9B is a computer simulation of the power density (proportional to $|E|^2$) at the operating resonant wavelength (λ=640 nm) for a PC surface (period=400 nm) operating with an external cavity gain of 0.01. This is a preliminary result that shows enhanced fluorescence excitation as high as $\sim 3 \times 10^8$, where similar simulations without external gain show enhancement factors of ~400× for enhanced excitation.

Preliminary computer simulations using Finite Difference Time Domain (FDTD) analysis, shown in FIG. 9b, support the idea that the gain provided by the external pump laser though the high Q lasing cavity can provide electric field stimulation of surface-adsorbed fluorophores well beyond what is obtained by ordinary illumination upon a glass surface or by simply illuminating a PCEF surface at the resonant coupling condition without external feedback. By incorporating a small amount of gain into an external mirror in the FDTD simulation, power densities substantially greater than the intensity of the illumination source (with $|E|^2=1$) are obtained, with the achievable gain determined by the laser diode gain, optical loss in the PC, and loss due to laser emission. Preliminary simulations suggest that PCEF in an ECL will result enhanced fluorophore excitation beyond the $|E|^2 \sim 400$ typically achieved with PCEF illuminated by a laser diode without an external cavity due to the high Q provided by the external cavity and the gain available from the laser diode.

In order to use the ECL to excite fluorescent dye molecules on the PC surface, we must choose an operating wavelength that corresponds to the excitation bandwidth of the dye. We have chosen to work with the dye Cy5 because it is one of the most commonly used labels for DNA molecules for gene expression analysis and for protein molecules in diagnostic assays. Cy5 is a popular dye for biological assays because it is excited by red (λ=633 nm) light from HeNe lasers. Of course, the principles described herein can be used for other dyes with other excitation wavelengths.

An embodiment for PCEF with an external cavity laser arrangement is shown schematically in FIG. 9a. Note that in this example, the measurements of binding interactions are made with a CCD camera 60 capturing images of the sensor surface. Measurements could alternatively be made via a photodiode detector, an avalanche photodiode detector, and a fluorescence microscope. Measurement of ECL wavelength shift is optional in this configuration. A commercially available diode (Sacher Lasertechnik SAL-0635-005, λ=630-640 nm) is used as the illumination source of an external cavity that has a PC biosensor 14 as the external mirror. Using methods demonstrated by our group previously (see A. Pokhriyal, M. Lu, V. Chaudhery, C.-S. Huang, S. Schulz, and B. T. Cunningham, "Photonic crystal enhanced fluorescence using a quartz substrate to reduce limits of detection," Optics Express, vol. 18, pp. 24793-24808, 2010), we contemplate construction of a low autofluoescence quartz substrate 21 using nanoimprint lithography to define the grating 23 pattern (Λ=400 nm, grating depth=25 nm, $TiO_2$ thickness=120 nm as used to obtain the results in FIG. 6) on a 1×3 $in^2$ microscope-slide sized surface. The PC is designed to provide a resonance at λ=640 nm in an air medium (overlapping the excitation band of the fluorophore present in the sample), when in an "as-fabricated" state, but the resonant wavelength will shift to greater values due to the addition of surface chemistry and immobilized capture molecules. Excitation of resonance and emission from the fluorophores is performed from below the PC surface using the ECL arrangement described previously, and fluorophore emission is captured from above the PC filter 14/20a by an electron-multiplied CCD camera 60 (EMCCD) through a wavelength-selective emission filter 62. To determine the PCEF enhancement factor, identical measurements are taken upon adjacent surfaces that contain a working PC and surface that contain the PC grating, but no $TiO_2$ thin film, and thus cannot produce a resonant reflection. A spectrometer will be used to verify that the ECL is able to tune itself to the resonant condition of the PC when different densities of Cy5-5 labeled proteins attached biomolecules are attached to the PC surface.

D. Bragg Fiber Embodiment (FIGS. 10-13)

Figure 10A:
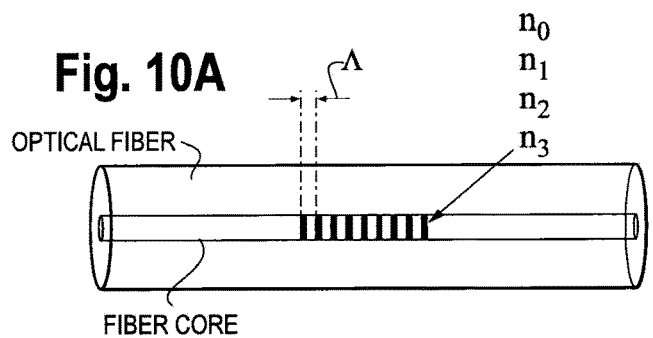
FIG. 10(a) is a schematic diagram of a Bragg optical fiber.
Figure 10B:
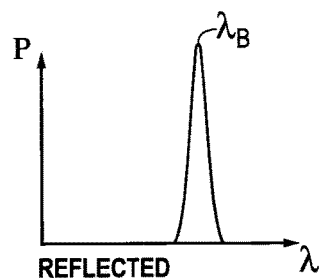
FIG. 10(b) is a plot of the reflection spectrum of a Bragg fiber.

Similar to photonic crystal structures, Bragg fiber reflects particular wavelength of light and transmits all others. Fiber Bragg gratings (as shown in FIG. 10(a)) are created by introducing periodic refractive index modulation into the core of a special optical fiber over a defined length. The index variation is generally introduced by UV exposure of fiber core which is composed of germanium doped material. The reflected wavelength ($\lambda_B$), called the Bragg wavelength, is defined by the relationship, $$\lambda_B = 2n_e \Lambda$$

where $n_e$ is the effective refractive index of the grating in the fiber core and Λ is the grating period. A typical reflection spectrum from Bragg fiber is shown in FIG. 10(b) with peak reflectance labeled as $\lambda_B$.

Figure 11A:
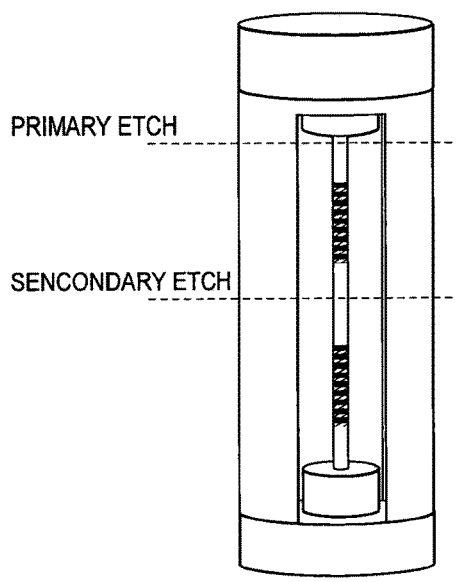
FIG. 11 is a diagram of a Bragg Fiber sensor.
Figure 11B:
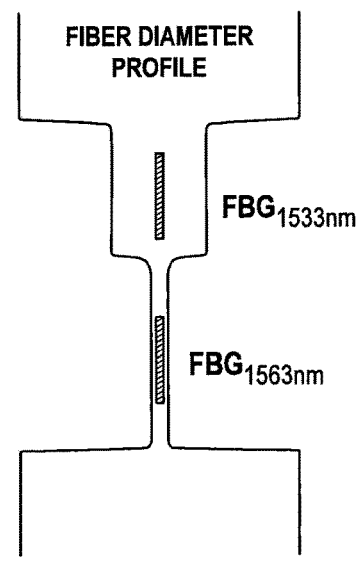

Bragg fibers can be constructed as biosensors. The evanescent wave in the Bragg fiber senses the change of the index of fraction following the binding of protein molecules to the surface of the fiber core. This change of index of refraction leads to a change of the Bragg wavelength, $\lambda_B$. In order to place chemicals and biomolecule close to the evanescence region of Bragg fiber, the cladding layer of fiber is removed and followed by a two-step etching process to shrink the diameter of the fiber core as shown in FIG. 11. See Geunmin Ryu, et al., "High Specificity Binding of Lectins to Carbonhydrate-Functionalized Fiber Bragg Gratings: A New Model for Biosensing Applications," IEEE Journal of Selected Topics in Quantum Electronics, Vol. 16, No. 3 May-June 2010.

Figure 12A:
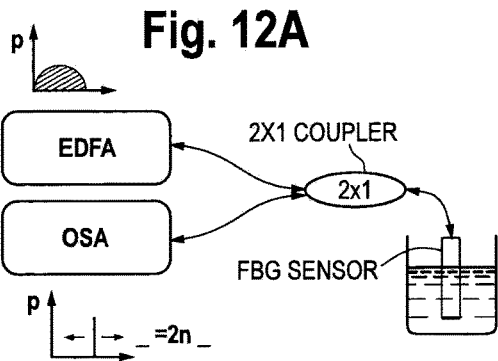
FIG. 12 is a diagram of a Bragg fiber sensor set-up and an example of the spectrum from the sensor.
Figure 12B:
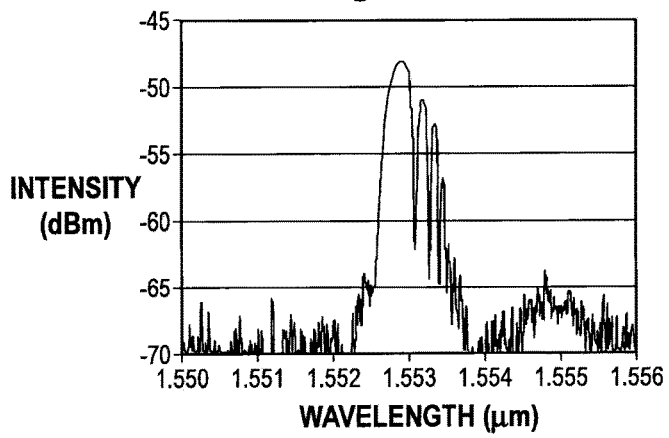

Used as a sensor, the processed Bragg fiber is inserted into target solution as shown in FIG. 12(a). The input broad light is coupled into Bragg fiber and reflected light (FIG. 12(b)) is analyzed by Optical Spectrum Analyzer to identify the peak reflection wavelength. By monitoring the shift of peak reflection wavelength, the surface absorption of biomolecule can be quantified.

Figure 13A:
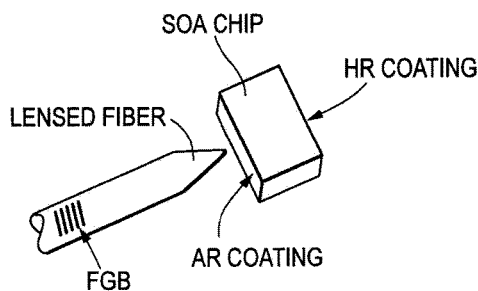
FIG. 13(a) is a diagram of a Bragg fiber external cavity laser.
Figure 13B:
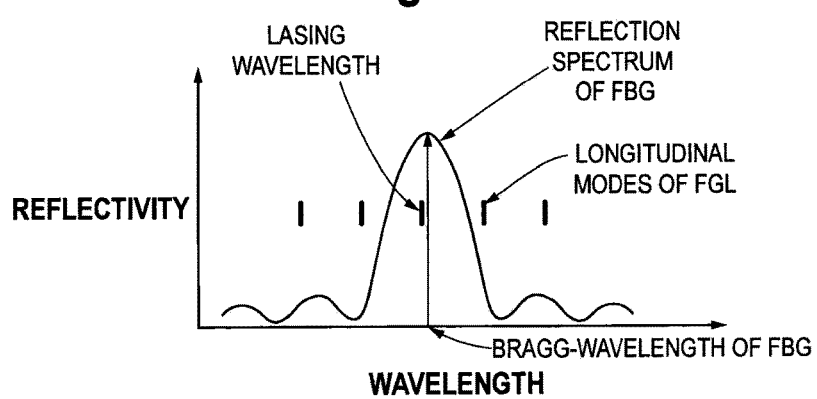
FIG. 13(b) is a diagram of the reflection and lasing spectra of a Bragg fiber external cavity laser.

Bragg fibers can also be used in the external cavity laser biosensor detection arrangements of this disclosure. Due to narrow bandwidth reflection, the Bragg fiber can be utilized as an end mirror for external cavity laser. See Jun-Ichi Hashimoto, et al., "Fiber-Bragg-Grating External Cavity Semiconductor Laser (FGL) module for DWDM Transmission," Journal of Lightwave Technology, Vol. 21, No. 9, September 2003. The setup and lasing mechanism of the Bragg fiber external cavity laser is shown in FIG. 13. The longitudinal mode of the external cavity nearest to the Bragg wavelength of the Bragg fiber is selected for the lasing wavelength. The laser wavelength follows the position of peak reflection wavelength, Bragg wavelength, of the Bragg fiber. If we compare spectrum of reflection spectrum of Bragg fiber and laser spectrum, it is obvious the linewidth is significantly reduced.

E. Bragg Stack Reflection Filters (FIG. 14)

Figure 14A:
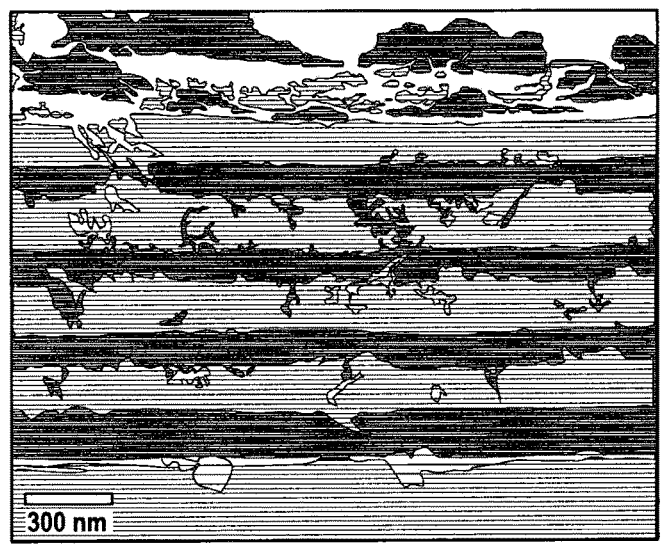
FIG. 14(a) is cross-sectional illustration of a Bragg Stack.
Figure 14B:
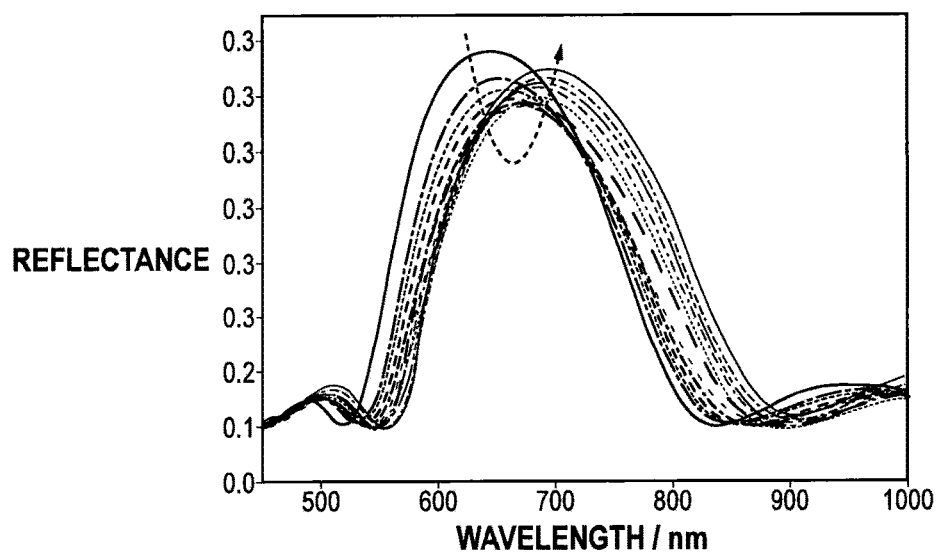
FIG. 14(b) shows the reflection spectra from a Bragg stack at different partial pressures of toluene vapors.

The cross-sectional structure of a Bragg stack is shown in FIG. 14(a). It can be characterized as a stack of alternating materials of high and low index of refraction. Due to Bragg reflection, a resonance peak is present in the reflection spectrum. The index of refractive of the surrounding medium determines the position of reflection peak. The Bragg stack is widely used as narrow band reflection mirror which can be found in most laser cavities, including external cavity laser. Nuria Hidalgo, et al., "Porous One-Dimensional Photonic Crystal Coatings for Gas Detection," IEEE Sensors Journal, Vol. 10, No. 7, July 2010.

Combined with an external cavity laser, it is possible to realize an ultra-sensitive Bragg fiber/stack biosensor. The sensing implementation is similar to the scheme shown in FIG. 12. The external cavity configuration will be used instead of broad band light excitation. Incorporated with external cavity laser, the Bragg fiber/stack sensor can also produce intense and narrow emission which enables the consequent sensor system to sense smaller mass variation in the vicinity of Bragg fiber core or Bragg stack.

We have also found that a semiconductor optical amplifier (SOA) is a desirable alternative to an antireflection coated laser diode for use in the biosensor detection arrangements of this disclosure. The SOA is very similar to the laser diode but it has antireflection elements on both ends. The SOA outputs light from its front and back facet, but light from the facet facing away from the sensor is coupled to fiber, reflected from a mirror, and send back into the SOA. The main advantage of a SOA is that it has a more flat and broad gain spectrum. With AR coatings on both faces, it does not lase on its own. The use of the SOA avoids having the ECL laser "hopping" between modes that are defined by the gain cavity length.

The appended claims are offered as further examples of the disclosed inventions.

We claim:

1. A biosensor system comprising:
a tunable lasing element that emits light at an emission wavelength within a wavelength range;
a resonant reflectance filter positioned relative to the tunable lasing element to reflect light at a resonant wavelength back into the tunable lasing element, wherein a binding or adsorption interaction of a biological material with a surface of the resonant reflectance filter causes a shift of the resonant wavelength, wherein the emission wavelength of the tunable lasing element is shifted by the shift of the resonant wavelength reflected by the resonant reflectance filter; and
a lens positioned to collimate the light from the tunable lasing element onto the resonant reflectance filter and focus reflection of light from the resonant reflectance filter back onto the tunable lasing element.

2. The biosensor system of claim 1, wherein the tunable lasing element comprises an antireflection coated laser diode having a first facet with high reflectance and a second facet having antireflection properties.

3. The biosensor detection arrangement of claim 1, wherein the tunable lasing element comprises a semiconductor optical amplifier.

4. The biosensor system of claim 1, wherein the resonant reflectance filter has a resonant wavelength that is tunable within a range that overlaps with the wavelength range of the tunable lasing element.

5. The biosensor system of claim 1, further comprising an instrument that receives the light emitted by the tunable lasing element and determines the wavelength or wavelength shift of the emitted light, wherein the instrument is selected from the group of instruments consisting of a spectrometer, an interferometer, and a monochrometer.

6. The biosensor system of claim 1, further comprising an optical fiber carrying light between the tunable lasing element and the resonant reflectance filter.

7. The biosensor system of claim 6, further comprising a second fiber carrying light between the tunable lasing element and a second resonant reflectance filter.

8. The biosensor system of claim 7, wherein the resonant reflectance filter is incorporated into a testing device having a plurality of discrete sample areas including a first sample area and second sample area, and wherein the first optical fiber illuminates the first sample area and wherein the second fiber illuminates the second sample area.

9. The biosensor system of claim 1, wherein the resonant reflectance filter is incorporated into a format selected from the group of formats consisting of a microplate, microarray, a slide, a device having a microfluidic channel, an internal surface of tubing, a test tube, a beaker, and a flask.

10. The biosensor system of claim 9, wherein the resonant reflectance filter comprises a photonic crystal.

11. The biosensor system of claim 10, wherein the photonic crystal comprises a substrate, a periodic grating of a first dielectric material formed on the substrate and a second dielectric material deposited on the periodic grating.

12. The biosensor system of claim 1, wherein the resonant reflectance filter comprises a Bragg stack comprising a stack of alternating materials of high and low index of refraction.

13. The biosensor system of claim 1, wherein the resonant reflectance filter comprises a Bragg fiber reflection filter.

14. A biosensor system comprising:
a tunable lasing element that emits light at an emission wavelength within a wavelength range;
a photonic crystal resonant reflectance filter positioned relative to the tunable lasing element to reflect light at a resonant wavelength back into the tunable lasing element, wherein a binding or adsorption interaction of a biological material with a surface of the photonic crystal resonant reflectance filter causes a shift of the resonant wavelength, and wherein the emission wavelength of the tunable lasing element is shifted by the shift of the resonant wavelength reflected by the photonic crystal resonant reflectance filter, the biological material including at least one bound fluorophore;

a lens positioned to collimate the light from the tunable lasing element onto the resonant reflectance filter and focus reflection of light from the resonant reflectance filter back onto the tunable lasing element; and a sensor that detects fluorophore emission from the surface of the photonic crystal resonant reflectance filter.

15. The biosensor system of claim 14, wherein the wavelength range of the tunable lasing element encompasses the absorption spectrum of the fluorophore.

16. The biosensor system of claim 15, wherein the wavelength range of the tunable lasing element is between 630 and 660 nm or between 850-880 nm.

17. The biosensor system of claim 15, wherein the sensor comprises a CCD camera.

18. The biosensor system of claim 15, further comprising an emission filter and an objective lens placed between the surface of the photonic crystal resonant reflectance filter and the sensor.

19. The biosensor system of claim 16, wherein the sensor is selected from the group of sensors consisting of a photodiode detector, an avalanche photodiode detector, a fluorescence microscope, and a camera.

* * * * *